United States Patent [19]

Robison et al.

[11] Patent Number: 4,618,583

[45] Date of Patent: Oct. 21, 1986

[54] METHOD OF PREPARING L-(+)-β-HYDROXYISOBUTYRIC ACID BY FERMENTATION

[75] Inventors: Robert S. Robison, North Brunswick; Michael G. Doremus, South Bound Brook, both of N.J.

[73] Assignee: E. R. Squibb & Sons, Inc., Princeton, N.J.

[21] Appl. No.: 672,984

[22] Filed: Nov. 19, 1984

[51] Int. Cl.[4] .............................................. C12P 7/42
[52] U.S. Cl. .................................................... 435/146
[58] Field of Search ......................................... 435/146

[56] References Cited

U.S. PATENT DOCUMENTS 3,553,081  1/1971  Goodhue et al. ............... 435/146
3,749,641  7/1973  Takahashi et al. ............... 435/47

FOREIGN PATENT DOCUMENTS 57-65192  4/1982  Japan .

Primary Examiner—Alvin E. Tanenholtz
Attorney, Agent, or Firm—Lawrence S. Levinson; Burton Rodney

[57] ABSTRACT

A method is provided for preparing L-(+)-β-hydroxyisobutyric acid by fermentation employing microorganisms of the species *Pseudomonas aeruginosa* and of the genus Protaminobacter such as of the species *Protaminobacter alboflavus,* and isobutyric acid and/or methacrylic acid and/or derivatives thereof as the substrate.

16 Claims, No Drawings

METHOD OF PREPARING L-(+)-β-HYDROXYISOBUTYRIC ACID BY FERMENTATION

FIELD OF THE INVENTION

The present invention relates to a method for preparing L-(+)-β-hydroxyisobutyric acid by subjecting the substrate, namely isobutyric acid or methacrylic acid or various derivatives thereof, to the oxidizing action of a microorganism of the species *Pseudomonas aeruginosa* or a microorganism of the genus Protaminobacter such as of the species *Protaminobacter alboflavus.*

BACKGROUND OF THE INVENTION

L-(+)-β-hydroxyisobutyric acid is used in the preparation of epi-captopril, which has the structure

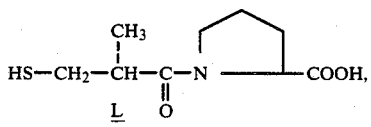

an angiotensin-converting enzyme inhibitor useful in the treatment of hypertension. It may also be used in preparing the monomer α-methacrylic acid which is used in preparing polyesters and other synthetic polymers.

Until now, L-(+)-β-hydroxyisobutyric acid has been prepared through the use of fermentation techniques. For example, U.S. Pat. No. 3,553,081 to Goodhue et al discloses that L(+)-beta-hydroxyalkanoic acid can be obtained by oxidizing an alkanoic acid containing 4 to 6 carbon atoms and at least one hydrogen on the beta-carbon atom, such as isobutyric acid, isovaleric acid and isocaproic acid with a microorganism selected from the group consisting of *Pseudomonas putida, Pseudomonas fluorescens, Arthrobacter oxydans, Arthrobacter crystallopietes* and Mycobacterium.

Japanese Kokai Pat. No. SHO 57 [1982] 65192 discloses a method of preparing L(+)-β-hydroxyisobutyric acid by employing microorganisms that have the ability to convert isobutyric acid or methacrylic acid or a mixture of the two to L-(+)-β-hydroxyisobutyric acid, such as microorganisms belonging to the genera Bullera, Candida, Cryptococcus, Debaryomyces, Dekkera, Hanseniaspora, Pachysolen, Pichia, Rhodosporidium, Rhodotorula, Saccharomyces, Schizosaccharomyces, Schwanniomyces, Sporobolomyces, Torulopsis, Trichosporon, Hansenula, Sporidiobolus, Nocardia, Streptomyces, Endomyces, Geotrichum, Helicostylum, Mucor, Paecilomyces, Fusarium, Bacillus, Brevibacterium, Corynebacterium, Enterobacter, Micrococcus, Sarcina and Kloeckera.

BRIEF DESCRIPTION OF THE INVENTION

In accordance with the present invention, there is provided a fermentation method for preparing the optically active L-(+)-β-hydroxyisobutyric acid, which method includes the steps of subjecting a substrate, such as isobutyric acid and/or methacrylic acid and/or derivatives thereof as will be seen hereinafter, to the action of a microorganism capable of converting one or more of the above substrates into L-(+)-β-hydroxyisobutyric acid such as *Pseudomonas aeruginosa* and/or one or more species of the genus Protaminobacter.

The above reaction may be carried out in several different ways. In a preferred embodiment, the microorganism is first cultivated in an aqueous nutrient medium, then the substrate is added to the resulting culture broth or to a suspension of cells obtained through the initial cultivation, and the mixture is then incubated aerobically.

In an alternative, the microorganism is cultivated aerobically in an aqueous nutrient medium containing all or a portion of the substrate so that cultivation of the microorganism and subjection of such portion of the substrate (present in the medium) to the action of the microorganism are carried out simultaneously. After a predetermined period and/or a predetermined concentration of product is obtained, the remainder of the substrate, if any, is added, and the fermentation is continued until a desired concentration of product is obtained.

DETAILED DESCRIPTION OF THE INVENTION

The microorganism preferably employed in carrying out the method of the present invention will be *Pseudomonas aeruginosa*, for example, ATCC #15523 or will be of the genus Protaminobacter, and preferably of the strain *Protaminobacter alboflavus,* for example, ATCC #8458. Other strains of the genus Protaminobacter which may be employed herein include *Protaminobacter candidus, Protaminobacter ruber* or *Protaminobacter thiaminophagus.*

Substrates which may be employed herein which will be converted to L-(+)-β-hydroxyisobutyric acid by the above microorganisms include, but are not limited to, isobutyric acid, methacrylic acid, the methyl ester and/or ethyl ester of each of isobutyric acid and/or methacrylic acids, isobutyryl chloride, isobutyl alcohol, one or more of its esters, such as isobutyl acetate, isobutyl formate, isobutyl isobutyrate or isobutyl methacrylate, isobutyl amine, isobutyl aldehyde, isobutyl amide or mixtures of any two or more thereof.

As indicated, for subjecting the substrate to the action of the microorganism, essentially two techniques are available. In the preferred method of the invention, the method is carried out in two steps, that is, cultivation of the microorganism first and then subjection of the substrate to the action of the microorganism.

The first step of the two-step process can be carried out by cultivating the microorganism in an aqueous nutrient medium and recovering the cells. The second step of the two-step process can be carried out by adding the substrate to a suspension of the recovered cells or to immobilized cells in suitable aqueous buffer or medium followed by incubating the resulting mixture aerobically for all or part of the reaction time at a pH from about 6 to about 9.5, and preferably from about 7 to about 8.5, and at a temperature of from about 20° to about 40° C. for about 12 to about 120 hours and preferably from about 48 to about 96 hours.

Since enzymes of microorganisms are involved in the reaction of the process of the present invention, the separated cells can also be subjected to various treatments, such as drying and homogenization, etc., before suspension in an appropriate aqueous medium in order to promote the enzyme reaction. Therefore, use of cells treated in various ways should be construed as being covered by the scope of the present invention.

In carrying out the alternative method wherein the microorganism is cultivated aerobically in an aqueous medium containing all or part of the substrate, reaction may be carried out by adding all or a portion of the substrate prior to growing the culture. The portion of substrate added to the culture prior to fermentation comprises from about 0.05 to about 0.2% and preferably from about 0.1 to about 0.15% by volume of the volume of aqueous medium to be used. The pH of the medium is adjusted, if necessary, to within the range of from about 5 to about 9.0, and preferably from about 6 to about 8.5, by adding strong inorganic base such as NaOH or KOH, while the reaction mixture is maintained at a temperature of from about 20° to about 40° C. The microorganism is cultivated aerobically and after a predetermined period of from about 12 to about 30 hours, and preferably from about 20 to about 25 hours, the remainder of the substrate is added. After addition of substrate is completed, the pH of the broth is adjusted within the range of from about 6 to about 9.5 and preferably from about 7 to about 8.5 by adding strong bases as described above. The fermentation is allowed to proceed for a total period of from about 40 to about 120 hours and preferably from about 48 to about 72 hours, until a concentration of product from about 0.2 to about 1.5%, and preferably from about 0.5 to about 1.5% by volume of the broth is achieved.

Another embodiment of the method of the invention includes the steps of adding all of the substrate material after the microorganism is cultured in the culture medium to provide an initial broth concentration of substrate of within the range of from about 1 to about 4% by volume and preferably from about 2 to about 3% by volume based on the total volume of the culture medium or broth, maintaining the pH of the broth between from about 6 to about 9.5 and preferably from about 7 to about 8.5 by adding strong base such as KOH or NaOH, while maintaining the broth at a temperature of from about 20° to about 40° C., and allowing fermentation to continue for a period within the range of from about 40 to about 120 hours and preferably from about 48 to about 72 hours until a peak concentration of product is achieved.

The fermentation media employed in the method of the invention includes a nitrogen source, a carbon/energy source, and optionally one or more inorganic salts for process control.

The nitrogen source will be present in an amount within the range of from about 0.1 to about 3%, and preferably from about 1 to about 2% by weight of the media. Examples of suitable nitrogen sources include casein hydrolysate, cottonseed meal, corn steep liquor, soybean meal, organic and inorganic compounds, such as $NH_4Cl$, $(NH_4)_2HPO_4$, $(NH_4)_2SO_4$, ammonia water, urea, amino acids, meat peptone, meat extract and hydrolysates of soy bean meal or any other comparable organic or inorganic N sources or their soluble derivatives.

The carbon/energy source will be present in the fermentation media in an amount within the range of from about 0.5 to about 5% and preferably from about 1 to about 3% by weight. Examples of suitable carbon/energy sources include starch, dextrin, maltose, lactose, glucose, glycerol, molasses, and the like, as well as organic acids, such as acetic acid, fumaric acid and lactic acid, alcohols such as methanol, ethanol and propanol, liquid hydrocarbons, such as n-paraffins and olefins, oils and fats and the like.

The fermentation media employed in the method of the invention may optionally include other conventional fermentation medium components such as one or more inorganic salts which aid in process control. Examples of such inorganic salts include, but are not limited to, $CaCO_3$, $CuSO_4$, $NaCl$, $ZnSO_4$, $FeSO_4$, $MgSO_4$, $MnSO_4$ or $Na_2HPO_4$ including hydrates thereof. The fermentation media may also contain one or more antifoam agents such as silicone antifoam.

A preferred fermentation medium formulation includes from about 1 to about 2.5% by weight of a nitrogen source, preferably a mixture of an organic and inorganic nitrogen, such as yeast extract, meat peptone, beef extract and ammonium phosphate, from about 1.0 to about 3% by weight of glucose as the carbon/energy source, optionally from about 0.01% to about 1% by weight of one or more inorganic salts, such as potassium dihydrogen phosphate and magnesium sulfate, and optionally from about 0.01 to 0.2% by weight of a silicone antifoam.

The L-(+)-β-hydroxyisobutyric acid product may be isolated from the culture broth or reaction mixture by subjecting the reaction mixture to filtration or centrifugation and then solvent extraction techniques. For example, in a preferred extraction method, the clarified culture broth or reaction mixture is acidified with a mineral acid, such as $H_2SO_4$ or HCl, to a pH within the range of from about 1 to about 4 and preferably from about 2 to about 3. Inorganic salt such as $(NH_4)_2SO_4$ or $Na_2SO_4$ is added to increase ionic strength of the broth or mixture, and the mixture is extracted with a water-immiscible solvent such as ethyl acetate, butanol or methyl isobutyl ketone. The desired product is obtained by distilling off the solvent and subjecting the residue to fractionation by, for example, high vacuum distillation at a temperature in the range of 100°–110° C., or by column chromatography on silica gel.

The following Examples represent preferred embodiments of the present invention. All temperatures are expressed in degrees Centigrade.

EXAMPLE 1

Preparation of L-(+)-β-Hydroxyisobutyric Acid Wherein Isobutyric Acid is Added to Cells of *Pseudomonas aeruginosa* in a Fermentation Broth 50 cc of the following medium was sterilized in a 250 cc Erlenmeyer flask after adjusting the medium to pH 7.5:

| | |
|---|---|
| Glucose - 1.0% | $MgSO_4.7H_2O$ - 0.04% |
| Yeast Extract - 0.5% | $ZnSO_4.7H_2O$ - 0.003% |
| Bacto-peptone - 1.0% | $FeSO_4.7H_2O$ - 0.0045% |
| Bacto Meat Extract - 0.5% | $CuSO_4.7H_2O$ - 0.00025% |
| $(NH_4)_2HPO_4$ - 0.65% | $MnSO_4.4H_2O$ - 0.0005% |
| $KH_2PO_4$ - 0.35% | NaCL - 0.005% |

(all of the above % being based on total volume of medium)

The above medium was inoculated with 2.5 cc of 48 hour old cell suspension of *Pseudomonas aeruginosa* which had been grown in a tube at 25° C. in 12 ml of the above medium. The inoculated flasks were then placed on a New Brunswick type shaker and incubated at 25° C. and at 300 RPM. After 23 hours, the equivalent of 1.0 ml of isobutyric acid (substrate) was added as a sodium salt solution and the pH was adjusted to 8.5 with sodium hydroxide.

The resulting mixture was incubated at 30° C. and the synthesis of hydroxyisobutyric acid was followed by HPLC analysis on the clarified supernatants of the fermentation broth. After 68 hours of incubation, 0.1% of hydroxyisobutyric acid was synthesized. The hydroxyisobutyric acid was extracted with ethyl acetate after the broth had been saturated with ammonium sulfate and adjusted to pH 2.4. The ethyl acetate was removed by distillation to an oily residue. The octyl ester of hydroxyisobutyric acid was prepared by treating the oily residue first with thionyl chloride and then with d-2-octanol.

The optical rotation of the hydroxyisobutyric acid synthesized was then determined by gas chromatographic analysis of the octyl ester. L-(+)-β-hydroxy isobutyric acid was synthesized.

EXAMPLE 2

Preparation of L-(+)-β-Hydroxyisobutyric Acid Wherein Isobutyric Acid is Added to Cells of *Protaminobacter alboflavus* in a Fermentation Broth Following the procedure of Example 1 except substituting the microorganism *Protaminobacter alboflavus* for *Pseudomonas aeruginosa*, and adding 1.0% calcium carbonate to the medium, the broth obtained from the culture of *Protaminobacter alboflavus* contained 0.05% hydroxyisobutyric acid.

EXAMPLES 3 TO 12

Preparation of L-(+)-β-Hydroxyisobutyric Acid Using Methacrylic Acid, Methyl Isobutyrate, Ethyl Isobutyrate, Methyl Methacrylate, Ethyl Methacrylate, Isobutyl Acetate, Isobutyl Formate, Isobutyl Isobutyrate or Isobutyl Methacrylate and Isobutyryl Chloride as Substrates with Cell Suspensions of *Pseudomonas aeruginosa*

Following the procedure of Example 1 except substituting ethyl isobutyrate (Example 3), methyl methacrylate (Example 4), ethyl methacrylate (Example 5), isobutyl acetate (Example 6), isobutyl formate (Example 7), isobutyl-isobutyrate (Example 8) or isobutyl methacrylate (Example 9), methacrylic acid (Example 10), methylisobutyrate (Example 11) and isobutyryl chloride (Example 12) for isobutyric acid, L-(+)-β-hydroxyisobutyric acid is obtained.

EXAMPLES 13 TO 22

Preparation of L-(+)-β-Hydroxyisobutyric Acid Using Methacrylic Acid, Methyl Isobutyrate, Isobutyryl Chloride, Isobutyl Alcohol, Isobutyl Amine, Isobutyl Aldehyde, Isobutyl Amide, Ethyl Ester of Isobutyric Acid, Ethyl Ester of Methacrylic Acid and Isobutyl-isobutyrate Following the procedure of Example 2 except substituting methacrylic acid (Example 13), methyl isobutyrate (Example 14), isobutyryl chloride (Example 15), isobutyl alcohol (Example 16), isobutyl amine (Example 17), isobutyl aldehyde (Example 18), isobutyl amide (Example 19), ethyl ester of isobutyric acid (Example 20), ethyl ester of methacrylic acid (Example 21) and isobutyl-isobutyrate (Example 22) for isobutyric acid, L-(+)-hydroxyisobutyric acid is obtained.

EXAMPLE 23

Preparation of L-(+)-β-Hydroxyisobutyric Acid Using Isobutyryl Chloride Substrate and *Pseudomonas aeruginosa*

10 Liters of the following medium is sterilized in a 14 liter glass fermentor after adjusting the pH of the medium to 7.5.

| Ingredient | Ingredient |
|---|---|
| Glucose - 1% | $ZnSO_4.7H_2O$ - 0.003% |
| Yeast Extract - 0.5% | $FeSO_4.7H_2O$ - 0.0045% |
| Bacto-peptone - 1% | $CuSO_4.7H_2O$ - 0.00025% |
| Bacto Meat Extract - 0.5% | $MnSO_4.4H_2O$ - 0.0005% |
| $(NH_4)_2HPO_4$ - 0.65% | NaCl - 0.005% |
| $KH_2PO_4$ - 0.35% | $CaCO_3$ - 1.0% |
| $MgSO_4.7H_2O$ - 0.04% | |

The glass fermentor is equipped with an agitator and sparger. The fermentor is operated at 30° C., and sterile air is supplied at 1 vol/vol medium/minute. The agitator speed is 500 rpm during the first 14 hours, and then 300 rpm until harvest. 100 ml of isobutyryl chloride is added after the medium has been sterilized and cooled to 30° C. and then the pH was adjusted to 7.3 with sodium hydroxide. 500 cc of a 24-hour broth culture of *Pseudomonas aeruginosa* is then used to inoculate the fermentor. After 23 hours, 100 ml of additional isobutyryl chloride is added, and the pH is adjusted to 8.35 with sodium hydroxide. At log 39, additional sodium hydroxide is added to adjust the pH to 8.5.

The synthesis of hydroxyisobutyric acid is followed by HPLC on clarified supernatants of the broth. After 43 hours of fermentation, the broth is found to contain 0.46% of hydroxyisobutyric acid. The hydroxyisobutyric acid is extracted with ethyl acetate after the clarified broth has been adjusted to a pH of 2.5 and saturated with ammonium sulfate. The ethyl acetate is removed by distillation. The oil residue is further purified by high vacuum distillation (0.2 mm) at 106°–108° C. The optical rotation of the distillate fraction recovered after high vacuum distillation established that the hydroxyisobutyric acid synthesized with this ester of isobutyric acid had the desired L(+)-rotation. Mass spectrometry indicated that the major component of this residue had a molecular weight of 104.

EXAMPLE 24

Preparation of L-(+)-β-Hydroxyisobutyric Acid Using Ethyl Methacrylate Substrate and *Protaminobacter alboflavus*

In this example, the procedure of Example 23 is followed except that ethyl methacrylate is used as the substrate in place of isobutyryl chloride and *Protaminobacter alboflavus* in place of *Pseudomonas aeruginosa* for the synthesis of L-(+)-β-hydroxyisobutyric acid.

The medium and operating conditions are essentially identical with those used in Example 23. All of the substrate, however, is added after 23 hours of fermentation to provide an initial broth concentration of ethyl methacrylate of 2.0%. After this substrate addition, the pH of the broth is maintained between 8.0 and 8.5 by the periodic addition of sodium hydroxide.

The synthesis of hydroxyisobutyric acid and the utilization of ethyl methacrylate is followed by HPLC. L-(+)-β-Hydroxyisobutyric acid is synthesized.

EXAMPLES 25 TO 31

Preparation of L-(+)-β-Hydroxyisobutyric Acid Using Methyl Isobutyrate, Ethyl Isobutyrate, Methyl Methacrylate, Isobutyl Acetate, Isobutyl Formate, Isobutyl Isobutyrate or Isobutyl-Methacrylate as the Substrate and *Pseudomonas aeruginosa*

Following the procedure of Example 23 except substituting methyl isobutyrate (Example 25), ethyl isobutyrate (Example 26), methyl methacrylate (Example 27), isobutyl acetate (Example 28), isobutyl formate (Example 29), isobutyl-isobutyrate (Example 30) or isobutyl-methacrylate (Example 31) for isobutyl chloride, L-(+)-β-hydroxyisobutyric acid is obtained.

EXAMPLES 32 TO 38

Preparation of L-(+)-β-Hydroxyisobutyric Acid Using Methacrylic Acid, Methyl Isobutyrate, Isobutyryl Chloride, Isobutyl Alcohol, Isobutyl Amine, Isobutyl Aldehyde and Isobutyl Amide as Substrate and *Protaminobacter alboflavus*

Following the procedure of Example 24 except substituting methacrylic acid (Example 32), methyl isobutyrate (Example 33), isobutyryl chloride (Example 34), isobutyl alcohol (Example 35), isobutyl amine (Example 36), isobutyl aldehyde (Example 37) and isobutyl amide (Example 38) for isobutyric acid, L-(+)-β-hydroxyisobutyric acid is obtained.

What is claimed is:

1. A method for producing L-(+)-β-hydroxyisobutyric acid, which comprises subjecting a substrate which is isobutyric acid, methacrylic acid, isobutyryl chloride, the methyl ester of isobutyric acid, the ethyl ester of isobutyric acid, the methyl ester of methacrylic acid, the ethyl ester of methacrylic acid, isobutyl alcohol, esters of isobutyl alcohol, isobutyl amine, isobutyl aldehyde, isobutyl amide or mixtures of two or more thereof, to the action of a microorganism of the species *Pseudomonas aeruginosa* or of the species *Protaminobacter alboflavus* to convert the substrate into L-(+)-β-hydroxyisobutyric acid in an aqueous medium, and recovering L-(+)-β-hydroxyisobutyric acid from the medium.

2. The method according to claim 1 wherein the substrate is the acetate ester of isobutyl alcohol, the formate ester of isobutyl alcohol, isobutyl isobutyrate, isobutyl methacrylate or mixtures of two or more thereof.

3. The method according to claim 1 wherein the substrate is isobutyric acid.

4. The method according to claim 1 wherein said microorganism belongs to the species *Pseudomonas aeruginosa*.

5. The method according to claim 1 wherein said microorganism belongs to the species *Protaminobacter alboflavus*.

6. The method according to claim 1 wherein the microorganism is cultivated aerobically in an aqueous medium containing the substrate.

7. The method according to claim 7 wherein the cultivation is carried out at a pH of from about 6 to about 9.5 and at a temperature from about 20° C. to about 40° C.

8. The method according to claim 1 wherein the substrate is added to a culture broth obtained by cultivating the microorganism in an aqueous medium and then the resulting mixture is incubated aerobically.

9. The method according to claim 8 wherein a small amount of said substrate is added in the aqueous medium when the microorganism is cultivated to induce enzymes of the microorganism.

10. The method according to claim 6 wherein microorganism is cultivated at a pH of from about 6.0 to about 9.5 and a temperature of from about 20° C. to about 40° C., the substrate is added and the mixture is incubated at a pH of from about 6.0 to about 9.5 at a temperature of from about 20° C. to about 40° C. for about 20 to 96 hours.

11. The method according to claim 1 wherein the substrate is added to a cell suspension prepared by cultivating the microorganism in an aqueous medium followed by centrifugation, suspending the cells in a buffered solution with the substrate and then incubating the resulting mixture aerobically for all or a part of the reaction time.

12. The method according to claim 11 wherein the separated cells are immobilized on a suitable carrier before contact with the substrate.

13. The method according to claim 11 wherein a small amount of said substrate is added in the aqueous medium when the microorganism is cultivated to induce the desired enzymes of the microorganism.

14. The method according to claim 11 wherein the microorganism is cultivated at a pH of from about 6.0 to about 9.5 and a temperature of from about 20° C. to about 40° C., the cells are then recovered, the substrate is added and the resulting suspension is incubated at a pH of from about 6.0 to about 9.5 and at a temperature of from about 20° C. to about 40° C. for about 20 to 96 hours.

15. The method according to claim 1 wherein L-(+)-β-hydroxyisobutyric acid is recovered from the aqueous medium by extraction with a water-immiscible solvent.

16. The method according to claim 15 wherein the water-immiscible solvent is butanol, methyl-isobutyl ketone, or ethyl acetate.

* * * * *

UNITED STATES PATENT AND TRADEMARK OFFICE
CERTIFICATE OF CORRECTION

PATENT NO. : 4,618,583

DATED : October 21, 1986

INVENTOR(S) : Robert S. Robison et al.

It is certified that error appears in the above-identified patent and that said Letters Patent is hereby corrected as shown below:

Column 8, line 7, "claim 7" should read --claim 6--.

Signed and Sealed this

Seventeenth Day of February, 1987

Attest:

DONALD J. QUIGG

*Attesting Officer*  *Commissioner of Patents and Trademarks*